US011365374B2

(12) United States Patent
Boels et al.

(10) Patent No.: US 11,365,374 B2
(45) Date of Patent: Jun. 21, 2022

(54) PRODUCT AND METHOD FOR REMOVAL OF BIOFILMS

(71) Applicants: S.A. REALCO, Louvain-la-Neuve (BE); INSTITUT NATIONAL DE LA RECHERCHE AGRONOMIQUE, Paris (FR)

(72) Inventors: Gauthier Boels, Brussels (BE); Gordon Blackman, Lasnes (BE); Christine Faille, Lille (FR); Yannick Lequette, Mont saint Eloi (FR); Martine Clarisse, Lys-lez-Lannoy (FR)

(73) Assignees: S.A. REALCO, Louvain-la-Neuve (BE); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 463 days.

(21) Appl. No.: 16/044,309

(22) Filed: Jul. 24, 2018

(65) Prior Publication Data

US 2018/0346849 A1 Dec. 6, 2018

Related U.S. Application Data

(62) Division of application No. 14/234,534, filed as application No. PCT/EP2010/065567 on Oct. 15, 2010, now abandoned.

(51) Int. Cl.
| | | |
|---|---|---|
| *C11D 3/386* | (2006.01) | |
| *C11D 3/48* | (2006.01) | |
| *A61L 2/18* | (2006.01) | |
| *C11D 3/00* | (2006.01) | |
| *C11D 11/00* | (2006.01) | |

(52) U.S. Cl.
CPC ............ *C11D 3/38618* (2013.01); *A61L 2/18* (2013.01); *C11D 3/0078* (2013.01); *C11D 3/386* (2013.01); *C11D 3/38636* (2013.01); *C11D 3/38654* (2013.01); *C11D 3/48* (2013.01); *C11D 11/0023* (2013.01)

(58) Field of Classification Search
CPC ............ C11D 3/38618; C11D 3/38654; C11D 3/0078; C11D 3/386; C11D 3/38636; C11D 3/48; C11D 11/0023; A61L 2/18
See application file for complete search history.

(56) References Cited

U.S. PATENT DOCUMENTS

| | | | |
|---|---|---|---|
| 3,676,352 A | | 7/1972 | Grimm et al. |
| 5,411,666 A | * | 5/1995 | Hollis ................. C02F 1/50 |
| | | | 210/632 |
| 6,100,080 A | | 8/2000 | Johansen |
| 6,537,955 B1 | * | 3/2003 | Raso ................. C11D 1/83 |
| | | | 510/218 |
| 2003/0205247 A1 | | 11/2003 | Lengling et al. |
| 2008/0293607 A1 | | 11/2008 | Jones et al. |

FOREIGN PATENT DOCUMENTS

| | | | |
|---|---|---|---|
| EP | 0590746 A1 * | 4/1994 | ............... C02F 1/50 |
| EP | 0831062 A1 * | 3/1998 | ............... C02F 1/50 |
| EP | 1 114 147 B1 | 11/2006 | |
| EP | 2 243 821 A1 | 10/2010 | |
| WO | 92/13807 A1 | 8/1992 | |
| WO | 98/26807 A1 | 6/1998 | |
| WO | 99/01535 A1 | 1/1999 | |
| WO | 91/98214 A1 | 12/2001 | |
| WO | 2006/031554 A2 | 3/2006 | |
| WO | 2008/112459 A2 | 9/2008 | |
| WO | 2008/153805 A2 | 12/2008 | |
| WO | 2008/153815 A2 | 12/2008 | |
| WO | 2009/085743 A1 | 7/2009 | |

OTHER PUBLICATIONS

PH. pH. http://hyperphysics.phy-astr.gsu.edu/hbase/Chemical/ph.html. 2002;1-5.*
Bremer et al. Laboratory scale Clean-In-Place (CIP) studies on the effectiveness of different caustic and acid wash steps on the removal of dairy biofilms. International Journal of Food Microbiology. 2006;106:254-262.*
International Search Report and Written Opinion for International Application No. PCT/EP2010/065567, dated Jul. 8, 2011, 21 pages.
Tokiwa, F., and T. Imamura, "Detergent Building Action of Uncharged Polymers in Relation to Their Molecular Weights," Journal of the American Oil Chemists Society 49(3):166-169, Mar. 1972.

* cited by examiner

*Primary Examiner* — Lynn Y Fan
(74) *Attorney, Agent, or Firm* — Christenson O'Connor Johnson Kindness PLLC

(57) ABSTRACT

Composition for the removal of biofilms present on a substrate, characterized in that it comprises at least one detergent component comprising a sequestrant and also a wetting agent and a dispersant and at least one enzymatic component containing at least one protease, at least one laccase and at least one polysaccharidase, method of implementation thereof and uses thereof.

23 Claims, 7 Drawing Sheets

PRODUCT AND METHOD FOR REMOVAL OF BIOFILMS

CROSS-REFERENCES TO RELATED APPLICATIONS

This application is a divisional of U.S. application Ser. No. 14/234,534, filed Apr. 21, 2014, which is a National Stage of International Application No. PCT/EP2010/065567, filed Oct. 15, 2010, the disclosure of each is hereby incorporated by reference in its entirety.

BACKGROUND

The invention relates to the field of biofilm removal. More specifically, the invention pertains to a composition and a method for removing biofilms.

Hygiene is of increasing importance in the food industry, in hospitals and particularly for surgery, in water purifying and desalinating plants, in the treatment of process water and in particular waste water of cooling towers, and for everyday needs such as contact lenses. When water circulates on a substrate, it is frequently observed that microorganisms freely circulating in the water may adhere to the surface. These microorganisms may then develop an adhesive extracellular matrix composed of polymer substances. A community of microorganisms adhering to a surface and encompassed in said matrix is called a biofilm. In general these biofilms are composed of bacteria.

It is unfortunately observed that this matrix is highly resistant and may form a barrier for agents acting against the microorganisms. Conventional treatments using sodium hydroxide and/or comprising different biocides do not act in sufficiently efficient manner since they do not penetrate the biofilm over its entire thickness or are inhibited by some constituent molecules of this matrix. Treatment is then only partly effective on the top surface of the biofilm. In addition, this film may also trap other microorganisms, particularly pathogenic microorganisms, than those initially present.

From WO09/26807 an enzymatic method is known for treating a biological film. In this method the biofilm is placed in contact with a cleaning composition containing one or more hydrolases to remove or release the biofilm layer from the surface. At a second step the biofilm is contacted with a bactericide disinfecting composition to destroy the bacterial cells present in the film. However, the simultaneous use of these two compositions is the cause of a degree of inactivation of some enzymes in the final mixture. The rapidity and efficacy of cleaning can therefore be improved by using a composition in which there is no inactivation of enzymes.

From document US2003/0205247 the use is also known of aqueous solutions containing enzymes to clean storage or fermentation tanks comprising one or more enzymes chosen from among the following: laccases, peroxidases, oxidoreductases, transferases, isomerases, lyases or ligases and a thickening agent with a foam amplifier. The field of action of the aforementioned solutions is relatively narrow, suitable for breweries since the chosen, illustrated enzymes are particularly known to be active on polyphenols which are the main constituents of fermentation residues, tannins and similar. The thickening agent is an agent modifying the viscosity and thixotropy of the solution, and is used for the purpose of allowing better adherence of the solution and/or of the foam onto the surfaces of the tanks to be treated. These solutions are not suitable for cleaning other tank or reservoir installations (e.g. comprising multiple piping or tubing) and are not suitable for removing other types of microorganisms and hence for a broad range of biofilms.

Document WO 92/13807 discloses the use of a composition allowing the removal of biomass and biofilms on substrates in aqueous systems i.e. in systems in which water is set in circulation or deposited. This type of system suffers from the presence of alkaline or acid biomass and biofilms due to the type of organisms generally present in this type of plant.

To solve this problem, document WO 92/13807 provides for the use of polysaccharidases and/or proteases and anionic surfactants such as SOS or DBS (sodium dodecylsulphate and dodecylbenzenesulphonic acid respectively) to remove biomass and biofilms.

Unfortunately, this type of composition is not efficient for a wide range of biofilms caused by various microorganisms and is of limited efficacy in removing biofilms.

As can be ascertained from the foregoing, these compositions always target a type of biofilm or particular microorganism and/or a particular application.

There is therefore a need for a composition and method capable of removing biofilms which are efficient within a reasonable time period, act on a wide class of biofilms produced by a wide class of microorganisms or groups of microorganisms, which are not harmful for the biofilm substrate and act both to prevent the development of biofilms and on longstanding biofilms having reached a stage of cohesion and major resistance.

To solve this problem, the present invention provides a composition for the removal of biofilms present on a substrate characterized in that it comprises:
- at least one detergent component comprising a sequestrant, a wetting agent and a dispersant,
- at least one enzymatic component containing at least one protease, at least one laccase and at least one polysaccharidase.

The forming of a composition comprising a detergent component and an enzymatic component containing at least one protease, at least one laccase and at least one polysaccharidase surprisingly allows a significant improvement in the rapidity and efficacy of the removal of a biofilm whilst being able to attack various types of biofilms. This composition allows the removal of all or almost all of the biofilm and can act on biofilms that are even mature or having an early development cycle and developed by multiple different species or microorganisms;

To date it is to be pointed out that no efficient composition can ensure the complete removal of biofilms present industrial plants. For example, in the food industry biofilms are inevitably formed (having regard to the richness of the surrounding medium). Biofilms have cyclic growth activity comprising a growth phase during which the microorganisms accumulate and a detachment phase during which entire pieces of biofilms become detached by erosion and under the effect of their own weight. When an industrialist is faced with this phenomenon, the production line should be stopped and different alternate washing cycles carried out with sodium hydroxide and numerous detergents and/or chemical and/or enzymatic cleaning agents since no polyvalent composition is available. Yet this represents numerous hours of work and loss of production yield.

As a result, in practice, production is not stopped and when the biofilm reaches the rupture phase the batches produced which are contaminated are discarded until the level of microorganism contamination of the food produced drops to a level acceptable by standards in force. In addition, it cannot be envisaged by industrialists to stock a particular detergent or enzymatic solution for every microorganism likely to contaminate the production line.

It is therefore most surprisingly that the present invention allows the providing of a fully polyvalent detergent composition which allows the removal of a broad spectrum of biofilms in various types of installations, does not require any particular precautions of use and is applicable both to tank type installations and to pipe type installations. The detergent removes a surface part of the biofilm and wets and/or swells the organic structures of the biofilm through the dispersing nature of the dispersant present in the detergent component. This therefore promotes the accessibility of the enzymatic component which weakens and degrades the matrix of the biofilm. This combined action of the three types of enzyme and of the detergent component promotes the accessibility of the composition to the deeper layers and allows optimal detaching of any type of biofilm whilst preserving the substrate.

In one particular embodiment of the invention, the composition is a solution with a pH of approximately between 8 and 11, preferably between approximately 9.5 and 10.5 and more preferably between approximately 9.5 and 10.

The pH value of the said composition has a major influence on its efficacy against a biofilm. A solution of said composition whose pH is approximately between 8 and 11 therefore surprisingly allows the removal of all or almost all of a biofilm.

Alternatively, said composition can be in solid form that is dissolved before use in a solvent so that when it is diluted in an aqueous phase, before application onto a biofilm, a solution is obtained whose pH is approximately between 8 and 11. In this case, the solid composition may comprise a basic compound and when it is placed in solution in the solvent and then diluted in an aqueous phase before application to the biofilm, a buffered solution is obtained having the composition of the invention with alkaline pH (value between 8 and 11).

In one advantageous variant of the invention, the composition is a solution designed so that when it is diluted in an aqueous phase before application to a biofilm, it forms a solution having a pH of approximately between 6.5 and 7.5, more particularly of about 7. In this manner, the pH of the solution of the composition is particularly suitable for the action of the enzymatic component, of laccase in particular. In addition, provision is made according to the invention to increase the pH at a subsequent application phase of the composition of the invention so as to obtain an alkaline pH particularly suitable for removing biofilm as mentioned above whilst maintaining optimum efficacy of the enzymatic component.

Alternatively, the said composition can be in solid form which is dissolved before use in a solvent to obtain a solution which is later diluted in an aqueous phase to obtain a cleaning solution having a pH of between approximately 6.5 and 7.5, preferably about 7.

Preferably, the said at least one enzymatic component comprises a proportion of protease(s) of between 10 and 50%, a proportion of laccase(s) of between 5 and 35% and a proportion of polysaccharidase(s) of between 5 and 20% by weight relative to the total weight of the enzymatic composition, the 100% of the enzymatic component optionally being reached using a conventional excipient or solvent e.g. an alcohol.

According to one preferred embodiment of the invention, the enzymatic component may contain between 1 and 10 proteases, preferably between 1 and 5 proteases, more preferably it may contain 2, 3, 4 or 5 proteases.

Non-limiting examples of protease enzymes belonging to class EC 3.4 and able to be used in the invention are the amino-peptidases (EC 3.4.11), dipeptidases (EC 3.4.13), dipeptidyl-peptidases and tripeptidyl-peptidases (EC 3.4.14), peptidyl-dipeptidases (EC 3.4.15), serine carboxypeptidases (EC 3.4.16), metallo carboxypeptidases (EC 3.4.17), cysteine carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo endopeptidases (EC 3.4.24), threonine endopeptidases (EC 3.4.25) and endopeptidases belonging to class EC 3.4.99.

Preferably, the proteases belong to class EC 3.4.21. The proteases are commercially available and are in different forms including powders, granules, suspensions, liquid solutions.

The laccases used in the invention belong to class EC 1.10.3.2. Laccases are enzymes containing copper and have the role of oxidizing a substrate in the presence of oxygen. More specifically, laccases are oxidoreductases which act with molecular oxygen as electron acceptor.

The at least one polysaccharidase used in the invention is an enzyme whose function is to break up the bonds in polysaccharides. Preferably, the at least one polysaccharidase may be an alpha-amylase, cellulose, hemi-cellulase, glucosidase, beta-glucanase or pectinase.

More preferably, the at least one polysaccharidase may be an alpha-amylase belonging to class EC 3.2.1.1, whose function is to break up (1-4)-alpha-glycosidic bonds in polysaccharides containing three or more alpha-(1-4)-D-glucose units. Preferably, the enzymatic component may comprise a proportion of laccase(s) of approximately 30%, a proportion of protease(s) of approximately 30%, a proportion of alpha-amylase(s) of approximately 10% by weight relative to the total weight of the enzymatic component, the 100% of the enzymatic component optionally being reached using a conventional excipient or solvent.

According to another preferred embodiment, if the enzymatic component comprises 2 proteases, the proportion of laccase(s) may be approximately 30%, the total proportion of proteases approximately 30%, the proportion of alpha-amylase(s) approximately 10% by weight relative to the total weight of the enzymatic component, the 100% of enzymatic component optionally being reached using a conventional excipient or solvent.

For example, the ratio between each protease may be between 1:2 and 2:1, preferably the ratio between each protease may be 1:1. The enzymes present in the enzymatic component have complementary action on a biofilm. For example, laccase is highly effective against contamination not attacked by alpha-amylase or proteases.

According to one preferred embodiment of the invention, the enzymatic component may be a solution or in solid form.

Preferably, the enzymatic component is a solution whose pH is between approximately 8 and 10. Preferably the enzymatic component is an aqueous solution whose pH may be between approximately 8.5 and 9.5; more preferably the pH may be approximately 9.0 for maximum maintaining of enzyme integrity.

Alternatively, the enzymatic component may be in solid form such as a lyophilisate, a powder, granules or in any other form allowing the solubilizing of said component in a solvent, which is later dissolved in said solvent. The solvent may be water or an aqueous, acid, basic, alcohol, buffered or neutral solution. The solubilized enzymatic component in this case can then subsequently be diluted in an aqueous solution optionally containing one or more compounds such as detergents for example to form the cleaning solution.

In one advantageous embodiment of the invention, the said at least one detergent component comprises a proportion of sequestrant of between 1 and 10% by weight relative to the total weight of the detergent component, which represents an optimum between efficacy, stability and cost.

The sequestrant is a chemical substance capable of forming complexes with mineral ions which it fixes in a form preventing the precipitation thereof via usual reactions. For example, the sequestrant may be ethylene-diamine-tetraacetic acid, glucono-delta-lactone, sodium gluconate, potassium gluconate, calcium gluconate, citric acid, phosphoric acid, tartaric acid, sodium acetate, sorbitol, a compound containing a phosphorus atom. Preferably, the sequestrant may be a phosphorus oxide such as a phosphonate, phosphinate or phosphate or a mixture thereof, or a salt thereof, an amine or amine oxide carrying in its structure at least one functional phosphine, phosphine oxide, phosphinite, phosphonite, phosphite, phosphinate, phosphinate or phosphate group, alone or in combination or a salt thereof.

More preferably the sequestrant may be a phosphonate or a salt thereof, an amine or amine oxide containing in its structure at least one functional phosphine, phosphine oxide, phosphinite, phosphonite, phosphite, phosphonate, phosphinate or phosphate group, alone or in combination, or a salt thereof. As a non-limiting example, the phosphonate may have the general formula $R^1(R^2-O)(R^3O)P=O$ in which $R^1$, $R^2$ and $R^3$ independently represent a hydrogen, alkyl, substituted alkyl, substituted or non-substituted alkyl-amino, substituted or non-substituted aminoalkyl, aryl or substituted aryl group. As a non-limiting example, the amine or amine oxide may comprise one, two or three substituents of general formula $CR^4R^5W$ in which $R^4$ and $R^5$ independently of each other represent a hydrogen, alkyl, substituted alkyl, substituted or non-substituted alkyl-amino, substituted or non-substituted aminoalkyl, aryl or substituted aryl group, and W is a phosphonate, phosphinate or phosphate group. The sequestrant may be in the form of a sodium, calcium, lithium, magnesium or potassium salt; preferably the sequestrant may be in the form of a sodium, calcium or potassium salt.

In one advantageous variant of the invention, the detergent component comprises a proportion of dispersant of between 1 and 10% by weight relative to the total weight of the detergent component.

The dispersant is therefore a chemical substance capable of improving the separation of the particles of a suspension to prevent agglutination, aggregation and/or decanting. The dispersant may be a polymer soluble or partly soluble in water such as polyethylene glycol for example or cellulose derivatives or a polymer comprising at least one acrylic acid or acrylic ester repeat unit. Preferably, the dispersant is a polymer comprising at least one acrylic acid or acrylic ester repeat unit of general formula —($CH_2$—CH—COOR)— in which R represents a hydrogen, alkyl or substituted alkyl, aryl or substituted aryl group. In particular, the dispersant is a polymer having a weight average molecular weight Mw of approximately between 500 and 10000.

More preferably, the dispersant is a polymer of acrylic acid. In particular, the dispersant may be a homopolymer of acrylic acid having a weight average molecular weight of approximately between 2000 and 6000.

In another embodiment of the invention, the detergent component comprises a proportion of wetting agent of between 1 and 15% by weight relative to the total weight of the detergent component.

The wetting agent is an amphiphilic chemical substance or a composition comprising said amphiphilic chemical substance, which modifies the surface tension between two surfaces. The advantage of the wetting agent is to promote the spreading of a liquid on a solid. The wetting agent may be anionic, cationic, non-ionic or zwitterionic. Preferably, the wetting agent may be an anionic or non-ionic wetting agent i.e. the hydrophilic part is negatively charged or does not comprise any distinct charge or may be a composition comprising an anionic wetting agent. More particularly, the wetting agent may be a sucrose ester or a composition comprising a sodium alkyl sulphate and an alcohol.

Advantageously, and preferably, in the detergent component of the invention, the said wetting agent is non-foaming when hot and is preferably chosen from the group formed by $C_6$ to $C_{10}$ sodium alkyl sulphates, $C_6$ to $C_{10}$ alcohol ether sulphates, $C_6$ to $C_{10}$ alkyl aryl sulphonates.

The fact that the wetting agent is a non-foaming wetting agent when hot allows the use thereof in installations comprising numerous pipes and tubes, thereby preventing the formation of foam without deteriorating the surfactant and/or emulsifying performance of the composition according to the invention, indeed the contrary. Evidently, the providing of an efficient detergent solution which does not generate foam limits the rinsing steps, which is particularly desirable in particular in installations having multiple piping and tubing.

As for the enzymatic component, the detergent component may be in the form of a solid to be dissolved in a solvent and/or in an aqueous phase or in liquid form.

When in solid form, it can either be directly placed in solution in the solution formed by the enzymatic component optionally already diluted in the aqueous phase, or it can be placed in solution in a solvent, prior to its dilution in the solution formed by the enzymatic component and the aqueous phase, or in the aqueous phase directly before dilution of the enzymatic component.

If the detergent component is in liquid form, the 100% of the detergent component are in general optionally reached using water, and prior to application to the biofilm it is diluted in an aqueous phase optionally already containing the enzymatic component.

Other forms of embodiment of the composition according to the invention are mentioned in the appended claims.

A further subject of the invention is a method for removing biofilms present on a substrate, characterized in that it comprises the following steps of:
a) providing a detergent component comprising a sequestrant, wetting agent and dispersant, and an enzymatic component containing at least one protease, at least one laccase and at least one polysaccharidase;
b) placing the detergent component in solution in an aqueous phase;
c) placing the enzymatic component in solution in the solution formed at step b) to form the solution of said composition according to the invention; or:
b') placing the enzymatic component in solution in an aqueous phase;
c') placing the detergent component in solution in the solution formed at step b') to form the solution of said composition according to the invention;
d) applying the solution of said composition formed at step c) or c') to the substrate for a predetermined period of time, in particular of between 15 minutes and 4 hours.

By "placing in solution" in the present invention is meant either the placing in solution of a solid compound in a liquid phase (solvent) or the dilution of a liquid compound in another liquid phase with which the liquid compound is miscible.

Alternatively, steps b) and c), or b') and c') can be conducted simultaneously to form a solution of said composition of the invention.

Preferably the method comprises the following steps of:
a) providing a detergent component containing a sequestrant, a wetting agent and a dispersant; and an enzymatic component containing at least one protease, at least one laccase and at least one polysaccharidase;
b) placing the detergent component in solution in water;
c) placing the enzymatic component in solution in the solution formed at step b) to form the solution of said composition of the invention;
d) applying the solution of said composition formed at step c) to the substrate for a predetermined period of time, preferably of between 15 minutes and 4 hours.

According to one preferred embodiment of the invention, the pH of the solution formed at step b) is between approximately 11.0 and 14.0, preferably between approximately 12.0 and 14.0 and more preferably between 12.8 and 13.8.

Advantageously, the pH of the solution of said composition formed at step c) or c') is between approximately 8 and 11, preferably between approximately 9.5 and 10.5, and more preferably between approximately 9.5 and 10.

In one variant of the invention, the pH of the solution of said composition formed at step c) or c') is between approximately 6.5 and 7.5, and a basic solution is added after the said application d) of the solution of said composition to the said substrate during said predetermined period of time so as to increase the pH up to about 8 to 9.

In this manner, when the composition of the invention is applied to the substrate, the prevailing pH is approximately between 6.5 and 7.5 enabling the laccase to benefit from optimal activity conditions. Next, the fact that the pH is increased up to about 8 or 9 enables the other enzymes in turn to reach their optimal efficacy. In this manner, they too will reach optimal activity conditions and as a result the biofilm will be removed in particularly advantageous manner since each enzyme present will find optimal conditions to perform its action and the biofilm will be detached and fully removed. In addition, since basic components are generally used in installations in which a biofilm may form, there is no addition of any exogenous component which could raise problems for validating the cleansing step. For example, to sanitize an installation, sodium hydroxide is frequently used and hence the addition of a substance of different nature is limited in the present invention.

Preferably the temperature of the solution of the detergent component formed at step b) or c') may be between approximately 35° C. and 50° C. According to one preferred embodiment of the invention, the composition of the invention is applied to a substrate coated with a biofilm for approximately 30 to 50 minutes, which represents a relatively short application time for such efficacy.

Preferably, the detergent compound comprises a proportion of sequestrant of between 1 and 10%, a proportion of dispersant of between 1 and 10%, and a proportion of wetting agent of between 1 and 15% by weight relative to the total weight of the detergent component. Preferably, the enzymatic component comprises a proportion of protease(s) of between 10 and 50%, a proportion of laccase(s) of between 5 and 35% and a proportion of polysaccharidase(s) of between 5 and 20% by weight relative to the total weight of the enzymatic component. More preferably, the at least one polysaccharidase can be an alpha-amylase.

With the present method, it is possible efficiently to remove the entirety of near-entirety of the biofilm, leaving on the substrate only isolated cells without the protection of the matrix. The subsequent action of a biocide allows the microbial strain to be destroyed. A subsequent disinfection phase will therefore be much more efficient after the application of a solution of the composition of the invention than after the application of a conventional cleaning phase not allowing this full removal of the matrix.

Therefore according to one preferred embodiment of the invention, the method further comprises a subsequent step to apply a biocide. For example but not limited thereto, the biocides may be of oxidizing type such as peracetic acid, hydrogen peroxide, potassium monopersulfate, sodium hypochlorite. According to the invention, the application of a biocide must be made after the application of the composition of the invention to prevent deactivation of the enzymes present in the said composition by the biocides.

Other embodiments of the method of the invention are mentioned in the appended claims.

The invention also relates to the use of a composition of the invention to remove biofilms present on a substrate, in particular to clean floors and surfaces, for clean-in-place or immersion cleaning. The composition can be used in closed installations or for immersion. Cleaning by immersion is particularly used to clean surgical equipment, contact lenses. The composition of the invention can be used to clean technical and process water circuits, air conditioning exchange systems or in the food industry.

Other forms of use according to the invention are mentioned in the appended claims.

The present invention also relates to a kit for the removal of biofilms present on a substrate, characterized in that it comprises:
at least one sample of detergent component in solution or in solid form, containing a sequestrant, a wetting agent and a dispersant; and
at least one sample of enzymatic component in solution or in solid form containing at least one protease, at least one protease, at least one laccase and at least one polysaccharidase.

Preferably the at least one polysaccharidase may be an alpha-amylase.

According to one preferred embodiment of the invention, the sample of the enzymatic component may contain between 1 and 10 proteases, preferably between 1 and 5 proteases, more preferably it may contain 2, 3, 4 or 5 thereof.

According to another preferred embodiment, the sample of the enzymatic component contained in the kit may comprise 2 proteases. Preferably, if the sample of enzymatic component comprises 2 proteases, the proportion of laccase(s) may be approximately 30%, the total proportion of proteases may be approximately 30% and the proportion of alpha-amylase(s) may be approximately 10% by weight relative to the total weight of the enzymatic component.

For example, the ratio between each protease may be between 1:2 and 2:1, preferably the ratio between each protease may be 1:1.

Preferably, the sample of the detergent component comprises a proportion of sequestering agent of between approximately 1 and 10%, a proportion of dispersant of between approximately 1 and 10% and a proportion of wetting agent between approximately 1 and 15% by weight relative to the total weight of the detergent component, optionally the 100% of the detergent component possibly being reached using water.

As an example, the sequestrant may be ethylene-diamine-tetraacetic acid, glucono-delta-lactone, sodium gluconate, potassium gluconate, calcium gluconate, citric acid, phosphoric acid, tartaric acid, sodium acetate, sorbitol, a compound containing a phosphorus atom. Preferably, the sequestrant can be a phosphorus oxide such as phosphonate, phosphinate or phosphate or a salt thereof, an amine or amine oxide or a salt thereof carrying in its structure at least one functional phosphine, phosphine oxide, phosphinite, phosphonite, phosphite, phosphonate, phosphinate or phosphate group.

More preferably the sequestrant may be a phosphonate or a salt thereof, an amine or amine oxide, or salt thereof, comprising in its structure at least one functional phosphine, phosphine oxide, phosphinite, phosphonite, phosphite, phosphonate, phosphinate or phosphate group. As a non-limiting example, the phosphonate may have the general formula $R^1(R^2O)(R^3O)P=O$ in which $R^1$, $R^2$ and $R^3$ are independently selected from the hydrogen, alkyl, substituted alkyl, substituted or non-substituted alkyl-amino, substituted or non-substituted aminoalkyl, aryl or substituted aryl groups. As a non-limiting example, the amine or amine oxide may comprise one, two or three substituents of general formula $CR^4R^5W$ in which $R^4$ and $R^5$ are independently selected from the hydrogen, alkyl, substituted alkyl, substituted or non-substituted alkyl-amino, substituted or non-substituted aminoalkyl, aryl or substituted aryl groups, and W is selected from the phosphonate, phosphinate or phosphate group. The sequestrant may be in the form of sodium, calcium, lithium, magnesium or potassium salt; preferably the sequestrant may be in the form of a sodium, calcium or potassium salt.

The dispersant may be a water-soluble or partly water-soluble polymer such as polyethylene glycol, cellulose derivatives or a polymer comprising at least one acrylic acid or acrylic ester repeat unit. Preferably, the dispersant is a polymer comprising at least one acrylic acid or acrylic ester repeat unit of general formula $—(CH_2—CH—COOR)—$ in which R may be a hydrogen, alkyl or substituted alkyl, an aryl or substituted aryl. In particular, the dispersant is a polymer having a weight average molecular weight Mw of between approximately 500 and 10000.

More preferably, the dispersant is a polymer of acrylic acid. In particular, the dispersant may be a homopolymer of acrylic acid having a molecular weight of between approximately 2000 and 6000.

The wetting agent may be anionic, cationic, non-ionic or zwitterionic. Preferably, the wetting agent may be an anionic or non-ionic wetting agent i.e. the hydrophilic part is negatively charged or has no distinct charge or it may be a composition comprising an anionic wetting agent More particularly, the wetting agent may be a composition comprising a sodium alkyl sulphate and an alcohol.

Advantageously, in the kit of the invention, the sample of the enzymatic component is an aqueous solution with a pH approximately between 8 and 10, preferably between approximately 8.5 and 9.5 and more preferably of about 9.0.

If the sample of the detergent component is a solution, the pH thereof is approximately between 11.0 and 14.0, more preferably between approximately 12.0 and 14.0, most preferably between 12.8 and 13.8.

In one variant of the invention, the sample of the enzymatic component is an aqueous solution whose pH is between approximately 6.5 and 7.5, preferably about 7.

Preferably, the kit of the invention also comprises a biocide.

Other embodiments of the kit according to the invention are mentioned in the appended claims.

Other characteristics, details and advantages of the invention will become apparent from the description below given as a non-limiting example with reference to the appended drawings and to the Examples.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

In the Figures, identical or similar elements carry the same references.

Example 1

Description of chosen test conditions: the tests were conducted as part of Clean-In-Place (CIP) procedure in a pilot industrial plant. The biofilms were developed on a planar face of a stainless steel cylinder perforated in its centre. This cylinder, once placed in a pipe having the same inner diameter as the outer diameter of the cylinder, causes sudden narrowing of the diameter thereof forcing liquid to pass through the central perforation. This stress leads to flow perturbations thereby creating dead zones on the surface of the cylinder. These dead zones promote the formation of a biofilm and hinder its mechanical detachment by the flow. They therefore typically represent zones that are difficult for biofilm removal.

Three different strains were used: *Pseudomonas fluorescens* (supplied by University of Cornell, Department of Food Science, Ithaca, N.Y., 14853, USA (Kathryn J. Boor, kjb4@cornell.edu); *Bacilfus mycoides* (supplied by the AFSSA laboratory in Maison-Alfort, France (Brigitte Carpentier, b.carpentier@lerpac.afssa.fr); *Bacillus cereus* (supplied by INRA, UR638, Processus aux Interfaces et Hygiene des Materiaux, Villeneuve d'Ascq, France (Christine Faille, Christine.faille@lille.inra.fr).

A growth medium was prepared as follows: powder meat extracts (Biokar) were dissolved in 0.1% distilled water and sterilized. 20 ml of inoculum with $5.10^7$ CFU/ml in a solution of Trypticase Soy Broth (TSB, Biokar) were deposited on the surface of the cylinders. These cylinders were incubated in a moist chamber at 30° C. for 2 hours to allow adhesion of the cells. The TSB solution was then removed and replaced by 20 ml of the meat growth medium and the cylinders were incubated 24 h at 30° C. The growth medium was then replaced by fresh meat medium and the cylinders were again incubated for 24 h.

Cleaning procedure comprised placing the cylinders contaminated with the biofilm in straight pipes of a pilot industrial plant cleaned by circulation (CIP cleaning). The treatment solutions were circulated for 30 minutes at 45° C. at a flow rate of 300 l/h. For two of the strains, tests were also performed at a flow rate of 600 l/h. Each test was repeated three times and a mean was determined.

The development and removal of the biofilms were monitored by microscope observation and by quantification of viable cells on the cylinders via a count on Trypticase Soy Broth medium after detachment of the cells.

Description of the Protocol for Preparation of the Composition

The detergent component was prepared by mixing in a determined volume of water: a phosphonate, a polyacrylate and an anionic wetting agent. The respective proportions in the detergent component were 3%, 4% and 3%. The pH of the solution was brought to 13.3 by dilution. A solution of the enzymatic component was prepared. This comprised a proportion of 30% proteases (EC 3.4.21), 30% laccase (EC 1.10.3.2) and 10% alpha-amylase (EC 3.2.1.1) and a conventional excipient.

The pH of the solution of the enzymatic component was brought to 9 by progressively adding a solution of potassium hydroxide. The solution of the composition according to the invention was prepared by adding the detergent component and enzymatic component to water. The solution of the said composition of the invention comprised 1% detergent component and 0.05% enzymatic component. The pH of the solution of said composition according to the invention was approximately 10.

Description of the Tests and Test Results

Test with the *Pseudomonas fluorescens* Strain

Figure 1:
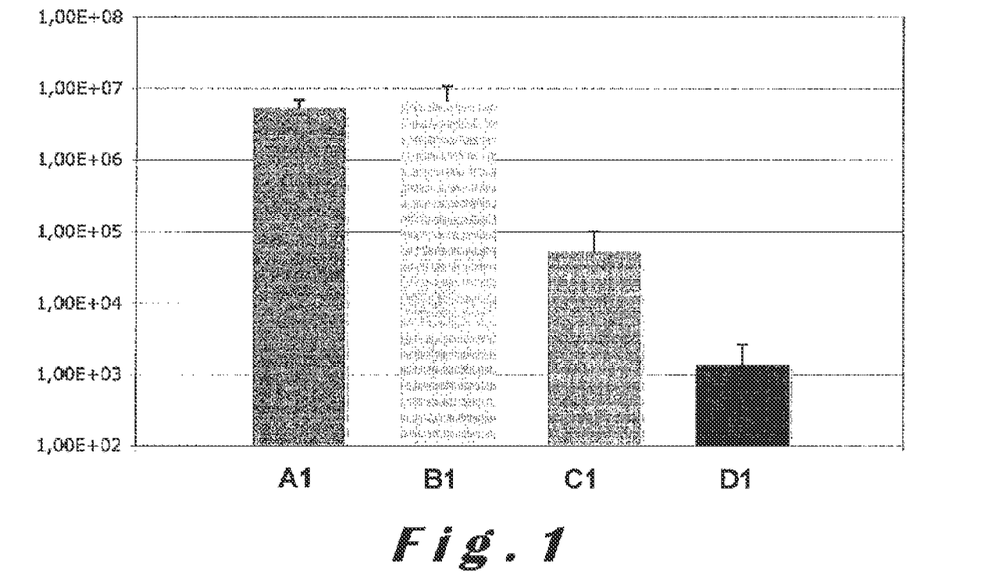
FIG. 1 is a graph showing the cell quantity of a *Pseudomonas fluorescens* strain on a substrate after application of different treatment solutions.

The graph given in FIG. 1 shows the quantity of biofilm present on the wall of the cylinder after application of treatment solutions following the conditions set forth above. The surfaces of the substrate were coated with a biofilm formed by the *Pseudomonas fluorescens* strain. The initial quantity of biofilm present before treatment is denoted A1 in FIG. 1.

Three solutions were compared: a solution solely containing water (B1); 0.5% sodium hydroxide solution (C1) and a solution of the composition of the invention (D1). The solutions were applied at a rate of 300 l/h and temperature of 45° C. Solution (B1) comprising water allowed evaluation of flow-induced mechanical detachment of the biofilms.

It was observed that the biofilm resisted mechanical detachment since the quantities of biofilm are identical (curves A1 and B1). The application of a solution of the composition of the invention allowed a major reduction in the biofilm (curve D1, $10^3$ CFU) compared with a sodium hydroxide solution (curve C1, $10^5$ CFU). The composition of the invention is therefore more efficient than a reference treatment (sodium hydroxide solution) on a biofilm resistant to mechanical detachment.

Figure 4:
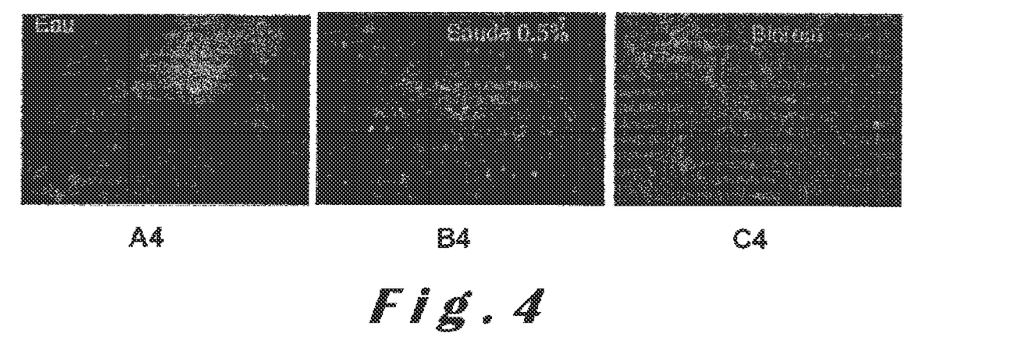
FIG. 4 gives images of the surface of a substrate, taken under epifluorescence microscopy, after application of different treatment solutions to said substrate coated with a biofilm of the strain *Pseudomonas fluorescens*.

FIG. 4 shows several images of the surface of a substrate, taken under epifluorescence microscopy, after application of the different treatment solutions at 300 l/h. Image (B4) shows the surface of the substrate subjected to a water solution, image (C4) shows the surface of the substrate subjected to a 0.5% sodium hydroxide solution and image (D4) shows the surface of the substrate subjected to a solution of the composition of the invention.

These data clearly show that the composition of the invention removed the entirety of the matrix of the biofilms (diffuse staining) leaving only isolated cells on the surfaces or small groups of cells distributed over a single layer unprotected by a matrix. The sodium hydroxide solution on the other hand did not allow complete removal of the matrix (diffuse staining) which still partly protects residual cells. A subsequent disinfection phase will therefore be much more efficient after application of a solution of the composition according to the invention.

Test with the *Bacillus mycoides* Strain

Figure 2:
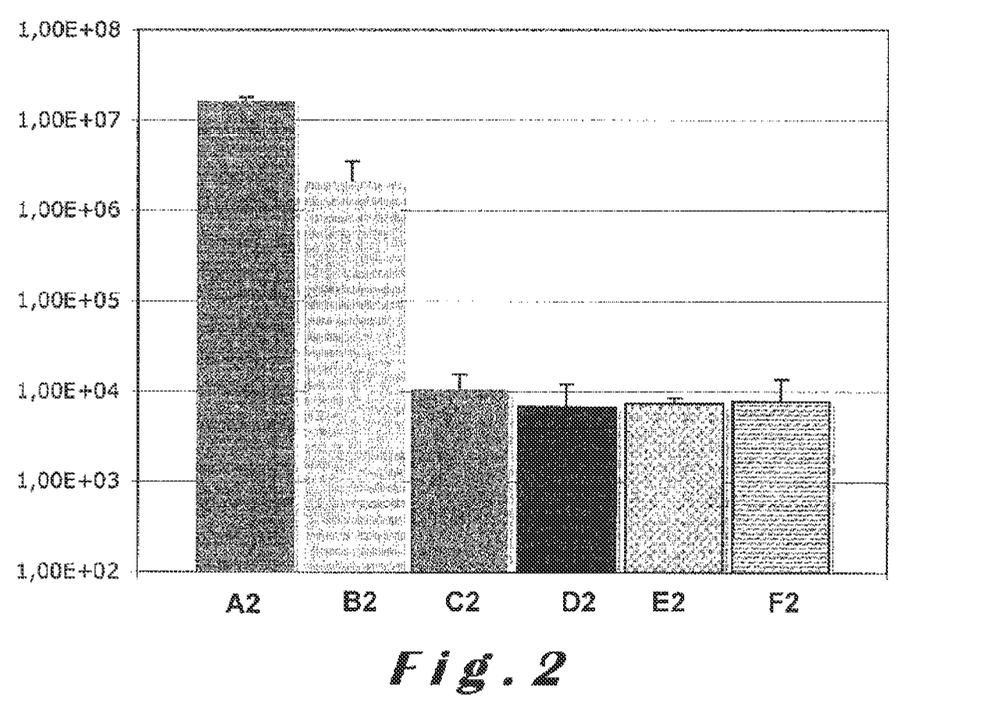
FIG. 2 is a graph showing the cell quantity of a *Bacillus mycoides* strain on a substrate after application of different treatment solutions.

The graph given in FIG. 2 shows the quantity of biofilm present on the wall of the cylinder after applications of treatment solutions following the conditions set forth above. The surfaces of the substrate were coated with a biofilm formed by the *Bacillus mycoides* strain. The amount of biofilm present before treatment is shown by curve (A2).

Five solutions were compared: a solution solely containing water (B2), 0.5% sodium hydroxide solution (C2), a solution of the composition according to the invention (D2 and F2) and a 2% sodium hydroxide solution (E2). The solutions A2-D2 were applied at a flow rate of 300 l/h whilst the solutions E2-F2 were applied at a flow rate of 600 l/h.

The biofilm of *Bacillus mycoides* is relatively sensitive to mechanical detachment its quantity being reduced by 90% with the application of solution (B2). Application of the solution of the composition of the invention (D2 and F2) showed equivalent performance to the sodium hydroxide solution (C2 and E2) whether the flow rate was 300 l/h or 600 l/h.

Figure 5:
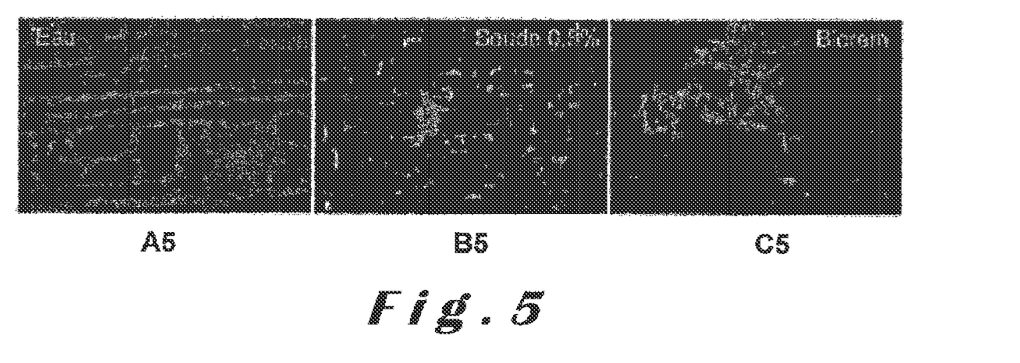
FIG. 5 gives images of the surface of a substrate taken under epifluorescence microscopy after application of different treatment solutions to said substrate coated with a biofilm of the strain *Bacillus mycoides*.
Figure 6:
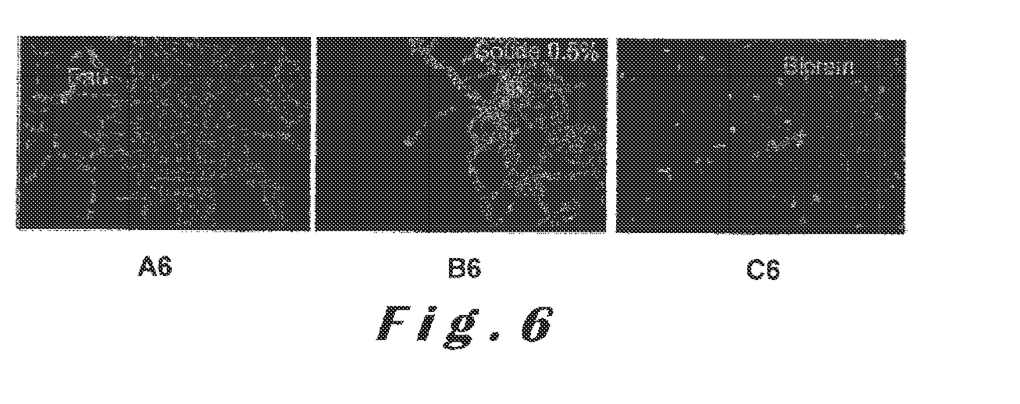
FIG. 6 gives images of the surface of a substrate taken under epifluorescence microscopy after application of different treatment solutions to said substrate coated with a biofilm of the strain *Bacillus cereus*.

FIG. 5 shows several images of the surface of the substrate taken under epifluorescence microscopy after application of the different treatment solutions at 300 l/h. Image (BS) shows the surface of the substrate subjected to a water solution, image (C5) shows the surface of the substrate subjected to a 0.5% sodium hydroxide solution, and image (D5) shows the surface of the substrate subjected to a solution of the composition of the invention.

These clearly show that the composition of the invention removed most of the matrix of the biofilms, only leaving isolated cells or small groups of cells distributed over a single layer unprotected by a matrix. The sodium hydroxide solution did not allow more efficient removal of the biofilm. The subsequent action of a disinfectant solution will therefore be more efficient if a solution of the composition of the invention is previously applied.

Test with the *Bacillus cereus* Strain

Figure 3:
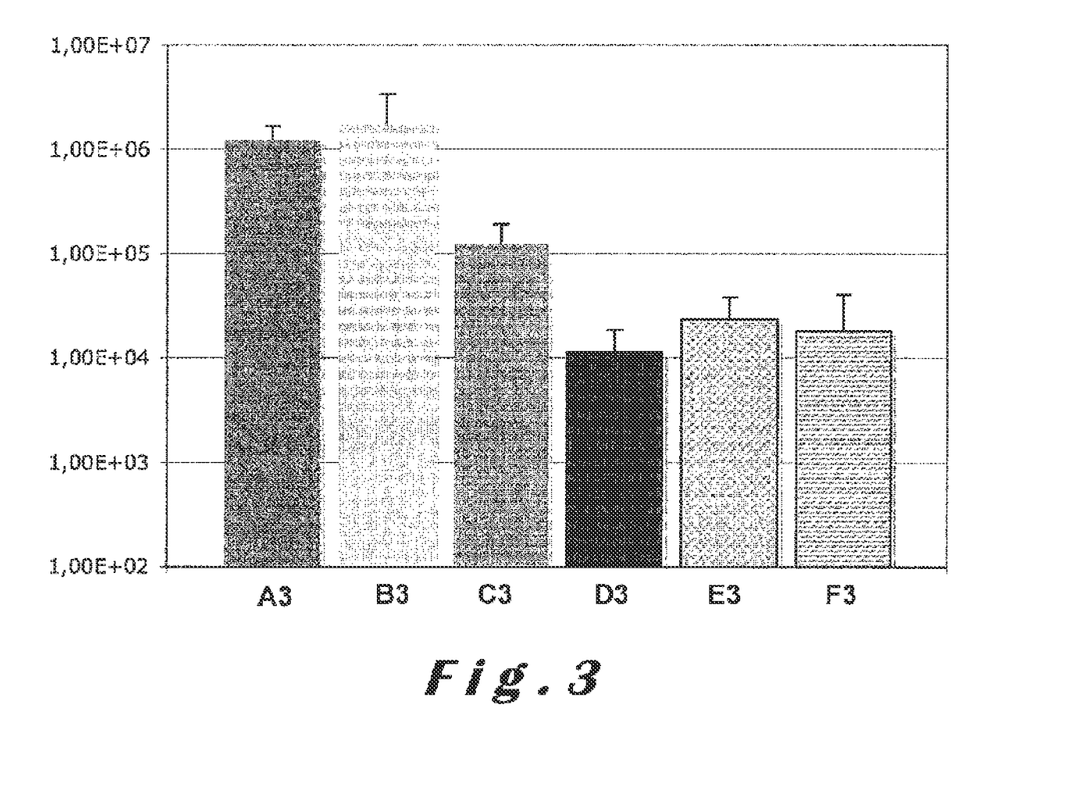
FIG. 3 is a graph showing the cell quantity of a *Bacillus cereus* strain on a substrate after application of different treatment solutions.

The graph give in FIG. 3 shows the amount of biofilm present on the wall of the cylinder after application of treatment solutions following the conditions set forth above. The surfaces of the substrate were coated with a biofilm formed by the *Bacillus cereus* strain. The amount of biofilm present before treatment is shown by curve A3.

Five solutions were compared: a solution solely containing water (B3), 0.5% sodium hydroxide solution (C3), a solution of the composition of the invention (D3 and F3) and a 2% sodium hydroxide solution (E3). Solutions B3, C3, D3 were applied at a flow rate of 300 l/h, whilst solutions E3 and F3 were applied at a faster rate (600 l/h). A faster flow rate has an influence on mechanical detachment.

The biofilm of *Bacillus cereus* fully resists mechanical detachment (curve A3 and B3). The composition of the invention showed greater efficacy at a flow rate of 300 l/h compared with a 0.5% sodium hydroxide solution (curve C3) and even at a flow rate of 600 l/h compared with a more concentrated sodium hydroxide solution (curve E3).

FIG. 6 shows several images of the surface of a substrate, taken under epifluorescence microscopy, after application of the different treatment solutions. Image (B6) shows the surface of the substrate subjected to a solution of water, image (C6) shows the surface of the substrate subjected to a 0.5% sodium hydroxide solution and image (D6) shows the surface of the substrate subjected to a solution of the composition according to the invention.

These images again show that the composition of the invention removes almost all the matrix of the biofilms, only leaving isolated cells or small groups of cells distributed over a single layer unprotected by a matrix.

The sodium hydroxide solution does not allow efficient removal of the biofilm. The disinfection phase of the substrate after the removal phase of the biofilm will therefore be more efficient after application of a solution of the composition of the invention for this removal phase.

The different tests performed in this Example demonstrate the efficacy of the composition of the invention in removing a biofilm from a substrate. The composition of the invention proves to be more efficient than a sodium hydroxide solution routinely used in the prior art. The composition of the invention also exhibits high efficacy against several types of biofilm derived from different bacteria. The composition of the invention therefore brings an efficient solution to the problems raised in the prior art and known to those skilled in the art.

Example 2

Tests were also performed on two industrial production lines (butter and margarine production). Stainless steel test coupons (8*1 cm) were placed for 15 days in production circuits having sporadic contamination. These coupons were therefore subjected to cycles of production and standard cleaning of the installations.

The presence of biofilm in the plant was determined by the development of a biofilm on the coupons. Specific Clean-In-Place procedure using the composition of the invention was applied in the plant in the presence of the contaminated coupons, and whose efficacy was demonstrated through the removal of the biofilms formed on the coupons.

The presence and size of the biofilms on the coupons were determined in a laboratory by staining the coupons and comparing the staining obtained with a visual scale (HYDROBIO®, BKG) and by observation under an optical microscope (40× and 100×).

Two cleaning protocols were tested: the first protocol was used as reference and corresponded to the application of solutions known in the prior art, the second protocol included the addition of a step to apply a solution of the composition according to the invention.

In particular Protocol I comprised the following steps: cleaning with water, alkaline cleaning, rinsing, sanitization (or disinfection) and final rinsing. Protocol 1 was applied every 32 hours for one week. Cleaning with water was applied for 15 minutes at a temperature of between 60 and 65° C. Alkaline cleaning allows pipes to be cleaned of organic matter present after a production cycle. This step was conducted using a 3.5% sodium hydroxide solution applied for 2*15 minutes at a temperature of between 70-75° C.

The sanitization step allows the removal of germs which may still be present but are unprotected by the matrix of the biofilm. This step entailed the application of a 1.5% solution of Deptil OX (HYPRED) for 2*15 minutes at a temperature of between 20 and 25° C. The Deptil OX solution contains a mixture of peracetic acid and hydrogen peroxide. The rinsing steps were performed for 15 minutes at a temperature of between 20 and 25° C.

Protocol II differed from Protocol I in that it comprised a specific cleaning step before the sanitization (or disinfection) step. In addition, Protocol II was only applied once.

The specific cleaning step consisted of the application of a solution of the composition according to the invention. This mixture was applied for 30 minutes at a temperature of between 40 and 45° C. The results obtained are given in Table 1.

TABLE 1

| | Quantity of biofilm after Protocol I ($g/m^2$) | Quantity of biofilm after Protocol II ($g/m^2$) |
|---|---|---|
| Production line 1 | 25 | <5 |
| Production line 2 | 25 to 35 | <5 |

Protocol I did not allow the limiting and prevention of growth of a biofilm despite the sanitization (disinfection) step. The biofilm which had formed on the stainless steel coupons at the heart of the installation was therefore very resistant. The application of Protocol II including a specific cleaning step with a solution of the composition of the invention allowed much more efficient removal of this biofilm (below the detection limit). Greater efficacy of the specific cleaning was therefore demonstrated which therefore provides an innovative solution to prior art problems.

Example 3

Tests allowing a comparison between optimal pH values were conducted.

Biofilms were developed on stainless steel coupons previously washed and sterilized. An inoculum of bacterium (*Pseudomonas aeruginosa*) was prepared by culture for 16 h in a 10% TSB medium (Tryptone Soy Broth). This pre-culture was diluted to obtain an optical density (OD) of 0.05 to 600 nm, and 500 μl of this solution were spread on each coupon. The coupons were incubated 48 h in Petri dishes held under moist conditions and placed in an oven at 30° C. After 2 hours, the bacterial solution was replaced by 500 µl of fresh 10% TSB medium. After 24 h, this culture medium was renewed.

The coupons were then cleaned and placed on metal rods separated by nuts. They were then placed in the cleaning solutions. The coupons were left immersed in the above-mentioned cleaning solutions for a total time of 30 minutes.

The cleaning solutions were the following:
1. Composition of the invention at pH 4.5, immersion for 30 minutes
2. Composition of the invention at pH7, immersion for 30 minutes
3. Composition of the invention at pH 9.7, immersion for 30 minutes The coupons were subsequently placed in test tubes containing 10 ml of TSB solution+0.5 Tween 80 for bacterial count The test tubes were incubated for 5 minutes on the table before being sonicated for 2 and a half minutes and vortexed for 30 seconds. The incubation, sonication and vortex steps were repeated.

The coupons were afterwards collected and the medium comprising the TSB solution+0.5 Tween was subjected to serial dilutions using peptone water (peptone water free of indole: preparation of 10 ml of 15 g/l dissolution. Dilution of 1 ml of this solution in 1 litre of sterile water); this medium was then spread on Petri dishes and incubated at 30° C. overnight before counting.

The biofilm was also stained as follows: the test coupons were drained and immersed in the staining solution for 10 minutes, selective for the proteins of the biofilm matrix. The coupons were then immersed in the different above-mentioned cleaning solutions 1 to 3, for a time of twice 10 minutes (the cleaning solutions were replaced between the two cleaning steps) before being left to dry in open air.

Results

At acid pH (4.5): a mat of bacteria developed on the surface of the Petri dishes, which indicated the presence of a large quantity of residual biofilm on the coupons.

At neutral pH (7): a mat of bacteria developed on the surface of the Petri dishes.

At alkaline pH (9.7): no bacteria present in the Petri dishes.

Figure 7:
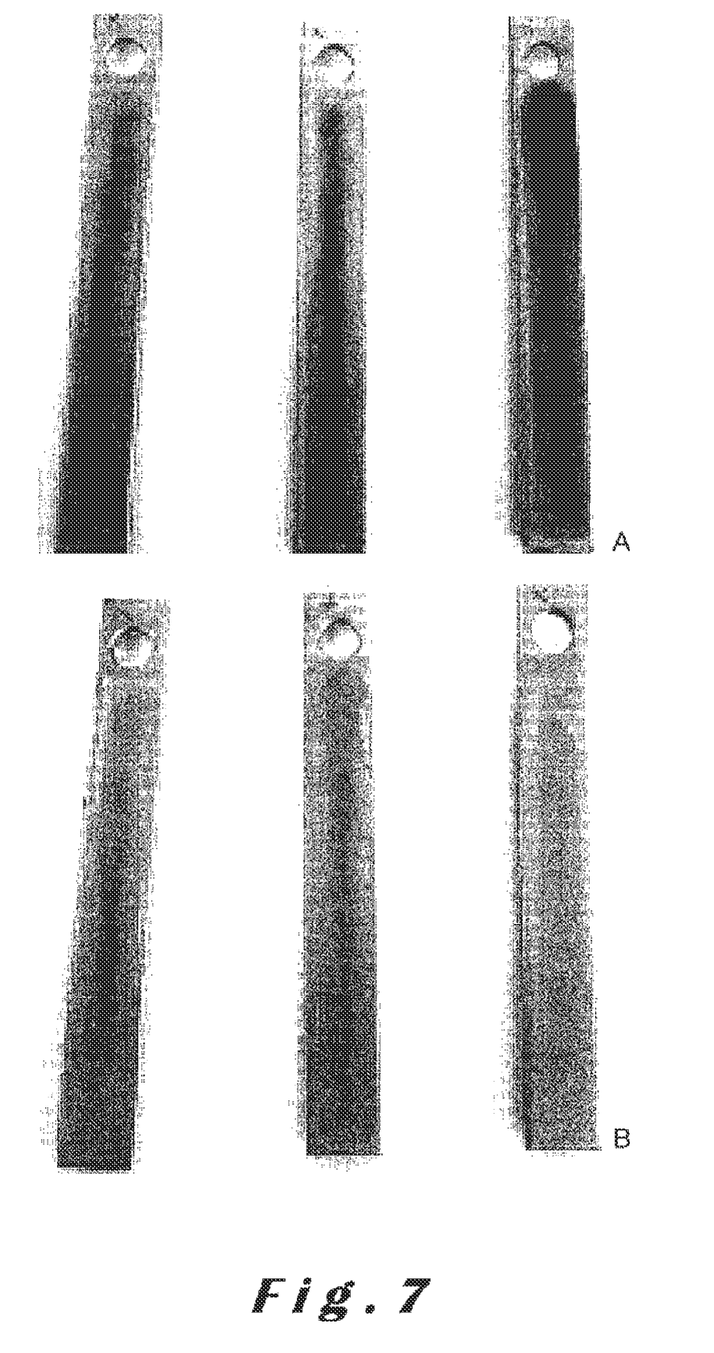
FIG. 7 gives the results of staining of biofilms before cleaning with cleaning solutions (A) and after cleaning with said solutions (B).

FIG. 7 gives the results of the staining of the biofilms. FIG. 7A illustrates the references before cleaning with treatment solutions 1 to 3, whilst FIG. 7B illustrates the steel coupons after cleaning with solutions 1 to 3 from left to right. As can be seen, cleaning at alkaline pH with the composition of the invention is clearly more efficient than at acid pH or at neutral pH, the biofilm developed on the coupon being fully detached with alkaline pH whereas it persists at other pH values.

Comparative Example

A test intended to determine the efficacy of four enzymes against three bacterial strains was conducted.

Figure 8:
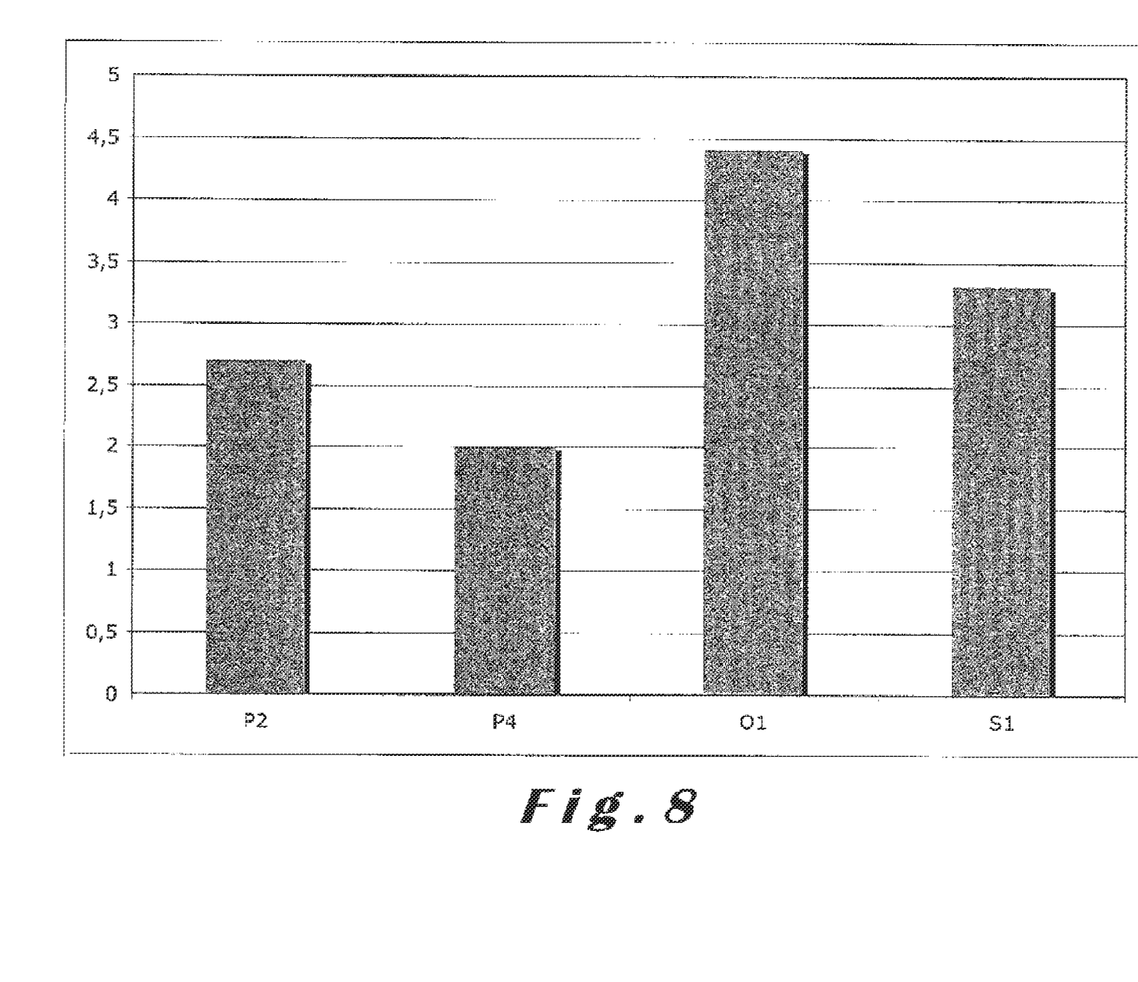
FIG. 8 is a graph showing the efficacy of four enzymes against biofilms derived from the strain *Chryseobacterium meningosepticum*.
Figure 9:
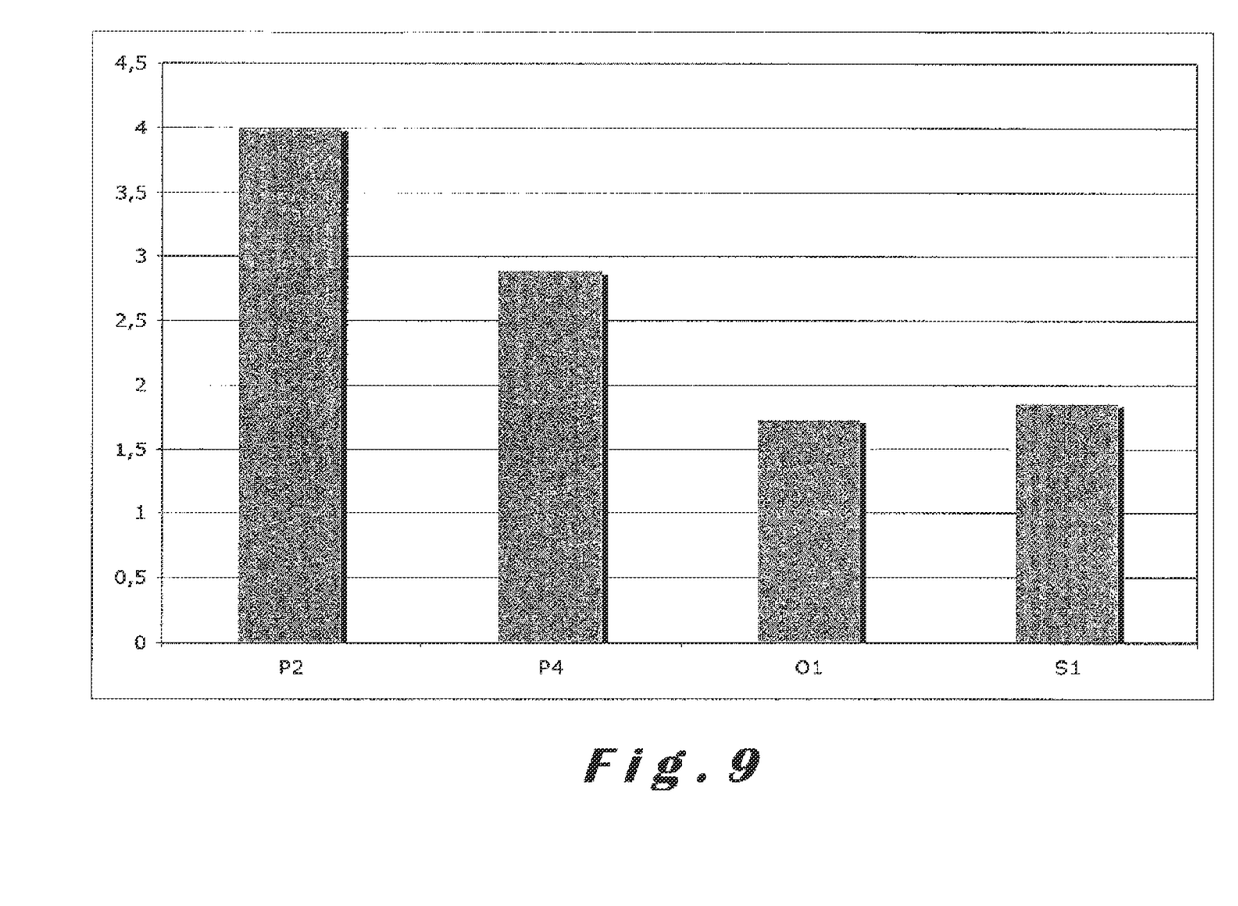
FIG. 9 is a graph showing the efficacy of four enzymes against biofilms derived from the strain *Bacillus Cereus*.
Figure 10:
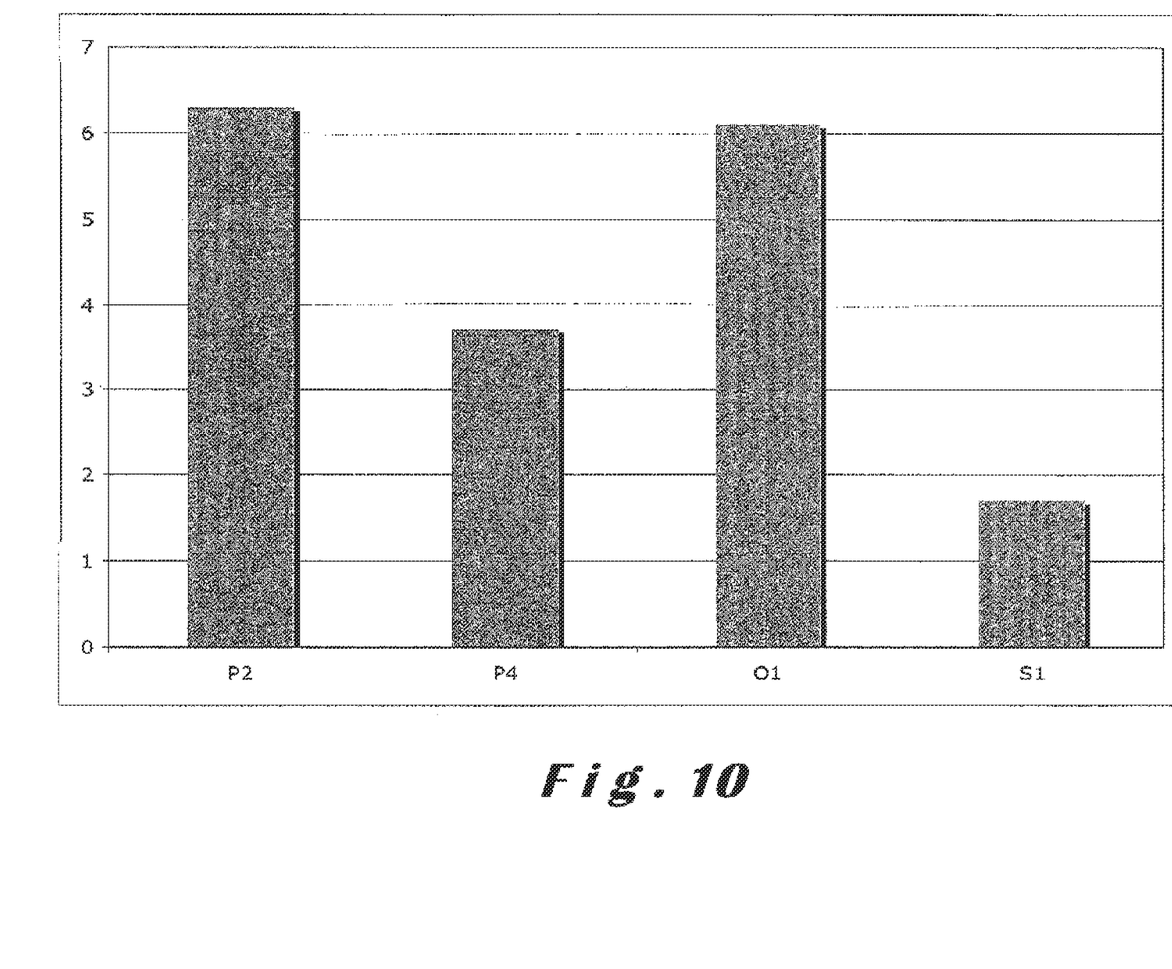
FIG. 10 is a graph showing the efficacy of four enzymes against biofilms derived from the strain *Pseudomonas fluorescens*.

The results of this test are given in FIGS. 8 to 10. Biofilms were formed on steel coupons (12) as in Example 3.

4 coupons were therefore produced for each bacterial strain (*Pseudomonas fluorescens*, *Bacillus cereus* and *Chryseobacterium meningosepticum*). The coupons were then rinsed with water before each being incubated with a cleaning solution respectively containing a first, a second protease, a laccase and a polysaccharidase for 30 minutes.

Tables 2 gives the results of the bacterial counts whilst FIGS. 8 to 10 show the logarithm of the results of bacterial count along the Y-axis and the type of enzyme used along the X-axis.

TABLE 2

| | Chryseobacterium meningosepticum | Bacillus cereus | Pseudomonas fluorescens |
|---|---|---|---|
| Initial contamination level | $2.0 \times 10^8$ | $7.0 \times 10^6$ | $2.0 \times 10^8$ |
| First protease | $4.0 \times 10^5$ | $7.0 \cdot 10^2$ | $1.0 \times 10^2$ |
| Second protease | $2.0 \times 10^6$ | $9.0 \times 10^3$ | $3.8 \times 10^4$ |
| Laccase | $8.0 \times 10^3$ | $1.3 \times 10^5$ | $1.6 \times 10^2$ |
| Amylase | $1.0 \times 10^5$ | $9.6 \times 10^4$ | $3.9 \times 10^6$ |

As can be seen, some bacterial strains are more sensitive to the action of the polysaccharidase and laccase, as is the case for *Chryseobacterium meningosepticum* (Gram−). As for *Bacillus Cereus* (Gram+), this is more sensitive to the combination of the two proteases whereas *Pseudomonas fluorescens* (Gram−) is more sensitive to the combination of the first protease and the laccase.

Evidently, the present invention is in no way limited to the above-described embodiments and numerous modifications can be made thereto without departing from the scope of the appended claims. For example, the fields of application of the compositions of the invention have proved to have particular use for cleaning by immersion e.g. in the hospital sector (cleaning laboratory equipment, surgical equipment), or by circulation within piping e.g. in the agri-food industry, in air conditioning installations, in water purifying and desalinating plants, for sailing vessel hulls and any type of immersed equipment, in washing machine, dishwasher circuits etc., or for soaking and circulation in piping.

The embodiments of the invention in which an exclusive property or privilege is claimed are defined as follows:

1. A method for removing a biofilm present on a substrate, comprising the steps of:
   (a) providing a detergent component comprising a sequestrant, a wetting agent and a dispersant, and providing an enzymatic component containing at least one protease, at least one laccase and at least one polysaccharidase;
   (b) placing the detergent component in solution in an aqueous phase;
   (c) placing the enzymatic component in solution in the solution formed at step (b) to form a solution comprising the sequestrant, the wetting agent, the dispersant, the at least one protease, the at least one laccase, and the at least one polysaccharidase; or
   (b') placing the enzymatic component in solution in an aqueous phase;
   (c') placing the detergent component in solution in the solution formed at step (b') to form a solution comprising the sequestrant, the wetting agent, the dispersant, the at least one protease, the at least one laccase, and the at least one polysaccharidase,
   wherein the pH of the solution formed at step (c) or (c') is between approximately 6.5 and 7.5; or
   optionally steps (b) and (c), or steps (b') and (c'), are conducted simultaneously to provide a solution comprising the sequestrant, the wetting agent, the dispersant, the at least one protease, the at least one laccase, and the at least one polysaccharidase;
   (d) applying the solution formed at step (c) or (c') to the substrate for a predetermined period of time to effect biofilm removal from the substrate; and (e) adding a basic solution after applying the solution formed at step (c) or (c') to said substrate during said predetermined period of time so as to increase the pH to about 8 to 9.

2. The method according to claim 1, wherein biofilm removal from the substrate removes microorganisms from the substrate.

3. The method according to claim 1 further comprising applying a biocide to the substrate.

4. The method according to claim 1, wherein applying the solution formed at step (c) or (c') to the substrate at step (d) comprises applying the solution to surface of a food production line.

5. The method according to claim 1, wherein applying the solution formed at step (c) or (c') to the substrate at step (d) comprises circulating the solution within piping.

6. The method according to claim 1, wherein the substrate is a floor or surface.

7. The method according to claim 1, wherein the method is a clean-in-place method.

8. The method according to claim 1, wherein the method is an immersion method.

9. The method according to claim 1, wherein the biofilm is a food industry biofilm and the substrate is a floor or surface in a food production line.

10. The method according to claim 1, wherein the predetermined period of time is between 15 minutes and 4 hours.

11. The method according to claim 1, wherein the at least one enzymatic component of the solution formed at step (c) or (c') comprises a proportion of the at least one protease of between 10 and 50%, a proportion of the at least one laccase of between 5 and 35%, and a proportion of the at least one polysaccharidase of between 5 and 20% by weight relative to the total weight of the enzymatic component.

12. The method according to claim 1, wherein the solution formed at step (c) or (c') comprises about 1% by weight detergent component relative to the total weight of the solution and about 0.05% by weight enzymatic component relative to the total weight of the solution.

13. The method according to claim 1, wherein said at least one polysaccharidase is an alpha-amylase.

14. The method according to claim 1, wherein said at least one detergent component comprises a proportion of sequestrant of between 1 and 10% by weight relative to the total weight of the detergent component.

15. The method according to claim 1, wherein said at least one detergent component comprises a proportion of dispersant of between 1 and 10% by weight relative to the total weight of the detergent component.

16. The method according to claim 1, wherein said at least one detergent component comprises a proportion of wetting agent of between 1 and 15% by weight relative to the total weight of the detergent component.

17. The method according to claim 1, wherein said dispersant is a polymer soluble or partly soluble in water and is selected from the group consisting of polyethylene glycol, cellulose derivatives, a polymer comprising at least one acrylic acid or acrylic ester repeat unit, a polymer comprising at least one acrylic acid or acrylic ester repeat unit of general formula —($CH_2$—CH—COOR)— where R represents a hydrogen, alkyl or substituted alkyl, aryl or substituted aryl group, a polymer of acrylic acid, and a homopolymer of acrylic acid having a weight average molecular weight approximately of between 2000 and 6000.

18. The method according to claim 1, wherein the dispersant is a polymer comprising at least one acrylic acid or acrylic ester repeat unit.

19. The method according to claim 1, wherein said dispersant is a polymer having a weight average molecular weight of between approximately 500 and 10000.

20. The method according to claim 1, wherein said wetting agent is selected from the group consisting of $C_6$ to $C_{10}$ sodium alkyl sulphates, $C_6$ to $C_{10}$ alcohol ether sulphates, and $C_6$ to $C_{10}$ alkyl aryl sulphonates.

21. The method according to claim 1, wherein the sequestrant is selected from the group consisting of a phosphonate, a phosphinate, a phosphate, a salt thereof, and a mixture thereof.

22. The method according to claim 1, wherein the enzymatic component is in the form of a dry solid, a powder, or a lyophilizate.

23. A method for removing a biofilm present on a substrate, comprising the steps of:
   (a) providing a detergent component comprising a sequestrant, a wetting agent and a dispersant, and providing an enzymatic component containing at least one protease, at least one laccase and at least one polysaccharidase;
   (b) placing the detergent component in solution in an aqueous phase;
   (c) placing the enzymatic component in solution in the solution formed at step (b) to form a solution comprising the sequestrant, the wetting agent, the dispersant, the at least one protease, the at least one laccase, and the at least one polysaccharidase; or
   (b') placing the enzymatic component in solution in an aqueous phase;
   (c') placing the detergent component in solution in the solution formed at step (b') to form a solution comprising the sequestrant, the wetting agent, the dispersant, the at least one protease, the at least one laccase, and the at least one polysaccharidase,
   wherein the pH of the solution formed at step (c) or (c') is between approximately 6.5 and 7.5; or
   optionally steps (b) and (c), or steps (b') and (c'), are conducted simultaneously to provide a solution comprising the sequestrant, the wetting agent, the dispersant, the at least one protease, the at least one laccase, and the at least one polysaccharidase;
   (d) applying the solution formed at step (c) or (c') to the substrate for a predetermined period of time to effect biofilm removal from the substrate; and
   (e) adding a basic solution after applying the solution formed at step (c) or (c') to said substrate during said predetermined period of time so as to increase the pH to obtain an alkaline pH between 8 and 11.

* * * * *